United States Patent [19]
Tailor et al.

[11] Patent Number: 5,529,826
[45] Date of Patent: Jun. 25, 1996

[54] FABRIC-FACED THERMOPLASTIC COMPOSITE PANEL

[76] Inventors: Dilip K. Tailor, 22 Torrance Woods, Brampton, Ontario L6Y 2T2; Mark F. Lang, 437 Watson Avenue, Oakville, Ontario L6J 3W1; Paul S. Hruska, 525 Meadows Blvd. #23, Mississauga, Ontario L4Z 1H2; Kevin J. McConnell, 25 Nash Road North #108, Hamilton, Ontario L8M 2P4, all of Canada

[21] Appl. No.: 196,925

[22] Filed: Feb. 15, 1994

[51] Int. Cl.$^6$ .............................. B32B 5/04; B32B 5/12; B32B 5/28
[52] U.S. Cl. .................... 428/110; 12/142 N; 12/146 D; 12/146 M; 12/146 S; 36/71; 36/145; 36/154; 36/DIG. 2; 156/176; 428/35.7; 428/36.1; 428/36.2; 428/111; 428/195; 428/196; 428/226; 428/230; 428/231; 428/232; 428/236; 428/238; 428/239; 428/246; 428/294; 428/542.8
[58] Field of Search ..................... 428/231, 232, 428/236, 238, 196, 36.1, 542.8, 110, 111, 226, 230, 239, 246, 294; 156/176

[56] References Cited

U.S. PATENT DOCUMENTS

| | | |
|---|---|---|
| 4,651,445 | 3/1987 | Hannibal . |
| 4,778,717 | 10/1988 | Fitchmun . |
| 5,082,701 | 1/1992 | Craven et al. . |

*Primary Examiner*—James C. Cannon
*Attorney, Agent, or Firm*—Duane, Morris, & Heckscher

[57] ABSTRACT

Polymer matrix composite materials containing a thermoplastic composite core bonded integrally with a fabric layer are provided. The fabric layer has a greater elasticity than the core, so that the fabric layer can conform smoothly to the core during thermoforming. This improvement has been demonstrated to improve aesthetic appearance and nearly eliminate wrinkling and distortion of the fabric layer when compared to conventional composite materials.

23 Claims, 3 Drawing Sheets

FABRIC-FACED THERMOPLASTIC COMPOSITE PANEL

FIELD OF THE INVENTION

This invention relates to polymer matrix composites, and more particularly, to thermoplastic composite materials that include a fabric facing for improving aesthetics and properties.

BACKGROUND OF THE INVENTION

Unreinforced engineering thermoplastics typically have tensile strengths that range from 8,000 to 15,000 psi. One popular engineering plastic, nylon 6/6, has a tensile strength of 12,000 psi and a tensile modulus of 500,000 psi. However, to compete with metals in applications ranging from automobiles to tennis rackets, plastics typically need to be reinforced to improve their mechanical properties.

Reinforcing thermoplastics and thermosets dramatically increases their strength. For example, short glass fibers at 30 wt. % loading can boost the tensile strength of engineering plastics by a factor of about two. Some advanced polymer-matrix composites (PMCs) have higher specific strength and stiffness than metals. Advanced composites reinforced with high modulus carbon fiber, for example, are known to have a tensile modulus of about 12.0 million psi and a tensile strength of 165,000 psi, but are much lighter than aluminum.

Polymer matrix composites are available in fiber-reinforced thermoset matrixes or fiber-reinforced thermoplastic matrixes. The thermoset matrixes typically include epoxy or polyester resins which harden through a catalytic process. The primary disadvantage of these systems has been that the resins include a hardener/catalyst to cure them, and this results in a limited shelf-life which may require refrigeration. This irreversible catalytic process requires a long curing cycle prior to hardening, and when these resins have finally set, they cannot later be thermoformed into a different configuration. Thermosets are also known to exhibit low ductility.

Because of their inherently faster processing time—no time-consuming curing or autoclaving—thermoplastic matrix composites are beginning to replace conventional thermoset composites. In the aircraft and aerospace sectors, current development work in thermoplastics is showing promising results for typical laminated structures, filament winding, and pultrusion. Several thermoplastic composite components have flown on United States Naval and Air Force jets in demonstration programs, and initial applications have included various access doors and outer wing panels on the Navy's F-18 fighter.

In order to obtain the maximum performance of thermoplastic composites in a given direction, continuous oriented fibers are lined in that direction in the composite. To improve the overall strength of the composite in all directions, these fibers can be alternated in succeeding layers to obtain multi-axial orientation and performance. The maximum performance of a thermoplastic composite is realized when each of the fiber filaments is wetted out by the resin, and when these wetted filaments are uniformly dispersed in the composite's cross-section.

The wetting of fiber filaments with thermoset resins is very efficient, since these resins tend to be low viscosity liquids. Thermoplastic resins usually require heat to melt them, and even then, they form a highly viscous melt, which does not readily flow to wet out the fiber filaments. Accordingly, special methods have been developed to produce unidirectional thermoplastic composites with good wet-out and uniform fiber dispersion.

One of these methods involves passing continuous fibers through a fluidized bed of thermoplastic resin powder. The powder penetrates into the web of the fibers, and the coated fibers are then heated and formed into a tape configuration. Alternatively, the fibers can be extruded through a melt of thermoplastic polymer, followed by shaping the coated fiber bundle. Still other methods of impregnating these fibers are to pass them through a solution in which a thermoplastic polymer powder is suspended, or sandwiching them between films of polymer. Other methods included passing the fiber through solvated resins, or through liquid partially polymerized or unpolymerized resins. The unidirectional tape can also be made using fibers of resin commingled with reinforcing fibers.

The end result of these impregnation methods is basically the same. A tape is produced in which there are continuous fibers in the axial or longitudinal direction, and these fibers are encapsulated within a given thermoplastic resin.

Fabrication of finished parts from fiber-reinforced thermoplastic composite unidirectional tapes has followed the especially labor-intensive process developed for fiber-reinforced thermoset composite unidirectional tapes. That is, these tapes are typically laid in successive laminated layers at predetermined angles to obtain the desired structural properties in a finished format of greater dimensions than the individual tapes. The tapes can be processed by hand, or with complicated, and often expensive, automatic tape laying machinery. Unlike fiber-reinforced thermoset tapes, which are more suitable for fabrication by these methods because they remain tacky until cured and can be held in a set position, lay-up fiber-reinforced thermoplastic tapes usually require that each tape be tacked, welded, or stitched in position before laying the next tape. These thermoplastic composite tapes can be difficult to mold since they are also known to be "stiff and boardy".

In order to produce a panel from these thermoplastic unidirectional tapes, techniques have been developed to hold them together prior to molding. One method disclosed in U.S. Pat. No. 5,082,701 suggests that the unidirectional fiber-reinforced thermoplastic tapes can be interlaced in an over-and-under relationship in a 0°/90° configuration. The interlaced material is then subjected to heat and pressure in single or multiple layers to form an integral panel. Alternatively, the tapes can be placed adjacently and seamed side-to-side, to produce a wide unidirectional sheet. In another method, the commingled resin/reinforcement fibers are woven into a fabric, and layers of this fabric are consolidated into a laminate by pressing or thermoforming. Laminates can also be produced by placing films of resin between layers of reinforcement fabric (woven or unwoven) and impregnating the fabric with the film by heat and pressure.

Preferably, the resulting sheets are placed on top of one another and then laminated together in a compression molding press. Additional polymeric films can be placed on top of the initial assembly, particularly over the woven sheets, to fill up the voids due to undulations of the woven pattern.

While such panels have successfully tackled the wet-out and uniform dispersion problems associated with impregnating fiber bundles with thermoplastic resin, there have been several drawbacks to these fabrication methods.

When the panels are thermoformed to extreme contours, as in deep drawing, there is a tendency for the panels to wrinkle rather than conform to produce smooth contours. This wrinkling occurs because the outside surface has continuous fibers which have little ductility, and they tend to distort and buckle when going over the contours in the die. In the case of a seamed-tape panel, the continuous unidirectional fibers also have a tendency to bundle up and appear as longitudinal wrinkles when molding certain shapes.

When such thermoplastic composite panels are subjected to flexing, the outermost unidirectional fibers on the top and bottom of the panels experience the maximum tensile and compressive stresses respectively while the fibers in the middle of the composite are stressed less, if at all. Since typical reinforcing fibers of carbon and glass have only about 1–4% elongation, the fibers on the top and bottom tend to fracture or buckle during static and dynamic loads. These fractures, along with the many seams and distortions in the fiber orientation and distribution can result in an outward appearance which can be generally unappealing, not to mention structurally defective.

In consumer applications, such as athletic shoes and shoe orthotic in-soles, where aesthetic appeal is critical, the presence of colors or patterns which beautify the panel are required. While currently produced woven-tape panels provide some pattern derived from the type of weave, and some colors halve been produced using colored unidirectional tapes, there is a limit to the available designs, particularly with respect to the width of the tape that can be used. Use of narrow tapes, such as 5 mm in width could provide interesting patterns, but the processes become very cumbersome and expensive, since large numbers of unwind creels would be necessary to produce a wide sheet. Also, if many colors are necessary, the process of feeding the warps and wefts in woven sheets of unidirectional tape becomes expensive and difficult.

In order to address the wrinkling and delamination problem associated with standard laminated thermoplastic composite structures, some have chosen to limit the fiber content to no more than about 33 vol. % of the total volume of the composite. See Fitchmun, U.S. Pat. No. 4,778,717, which is hereby incorporated by reference. Fitchmun describes a composite having a thermoplastic core and fibrous layers adhered to the thermoplastic core, whereby the total fiber volume is less than ⅓ of the total volume of the composite. He further teaches that fiber volume fractions greater than 50% of the total volume "completely resist" molding into a desired shaped, and if molded, contribute to rippling and buckling of portions of the surface of the resulting molded structure. He suggests that the buckled portions result from the failure of the fibrous material to properly move relative to the core which produces a locking of the sheet material during molding. This locking can only be relieved, he states, by severe folds.

Unfortunately, since Fitchmun does not teach a large enough loading of fiber reinforcement in his thermoplastic composites for many PMC applications, the typical improvements in modulus and tensile strength derived from greater fiber volume fractions are not obtainable with his composite. More importantly, Fitchmun teaches a composite structure in which the fiber reinforcement is only on the surface on each side of the plastic core. He uses the core of thermoplastic material between the two fabric layers to allow the two fabric layers to move independently of each other during thermoforming. He explains that the independent freedom of movement enables the layers of fabric to be molded into complex shapes.

Accordingly, there appears to be a need for a thermoplastic composite material that, instead of employing a fabric-wrapped core material, employs a true solid composite with a homogeneous distribution of the fibers throughout its body, and which can be molded into a smooth finished article without distortion or wrinkling, while simultaneously retaining a high modulus and tensile strength. There is also a need for a thermoplastic composite material which can be provided with a greater degree of aesthetic appeal for consumer applications.

SUMMARY OF THE INVENTION

Polymer matrix composites are provided by this invention which are suitable for thermoforming to form molded articles. These composite materials include a thermoplastic composite core and a fabric layer integrally bonded to the core. In order to minimize buckling and wrinkling of the fabric layer as it attempts to conform to the composite core during thermoforming, the fabric layer is provided with greater elasticity than the core so that it can stretch and conform smoothly to the core as it is shaped.

The thermoformable thermoplastic composite materials of this invention overcome the problems cited above for conventional composites. Due to the inherent nature of the fabrics of this invention, there is some elasticity present in the fabric. The type of fibers used for these fabrics such as polyester and nylon, also have inherent elasticity, which facilitates their suitability for the molded applications. Preferably, the elasticity is at least 5% greater than the elasticity of the composite core at a given load. During molding onto contours of a mold, this retained elasticity allows the fabric to conform smoothly without wrinkling or buckling prior to being fixed to the core by molten resin. The fabrics of this invention are capable of producing much smoother surfaces, than woven tapes of composite material which trap their fibers in the oriented state with impregnated resin. The fibers of the fabrics of this invention are free to adjust to deformation pressures and, i.e. there is some "slackness" present in them prior to thermomolding.

In more preferred embodiments of this invention, a thermoplastic composite core is provided which includes at least two laminated thermoplastic sheets including unidirectional fibers having a first and a second orientation. A woven fabric layer is bonded to the thermoplastic composite core by a resin, such as a resinous adhesive. This woven fabric layer is more elastic than the core so that upon thermoforming, the fabric layer conforms smoothly to the core without wrinkling.

Woven fabrics are especially suited to this invention, since the alternative insertion of the fibers over one another in the woven pattern inherently provides some measure of pliability and elasticity. Additionally, the woven fabric can be embedded into the thermoplastic resin of the core so as to intimately contact or restrict the underlying fibers. In the preferred constructions, the fabric aids in preventing undue movement of the fiber reinforcement in the thermoplastic composite core to avoid buckling and wrinkling in the final molded article.

This invention can also employ fabrics having a printed pattern so as to greatly improve the aesthetic appearance of the resulting molded article for consumer products. Ordinary natural and synthetic fibers can be employed with the variety of colors and patterns currently available in the textile industry.

BRIEF DESCRIPTION OF THE DRAWINGS

The accompanying drawings illustrate preferred embodiments of the invention so far devised for the practical application of the principles thereof, and in which.

DETAILED DESCRIPTION OF THE INVENTION

Figure 1:
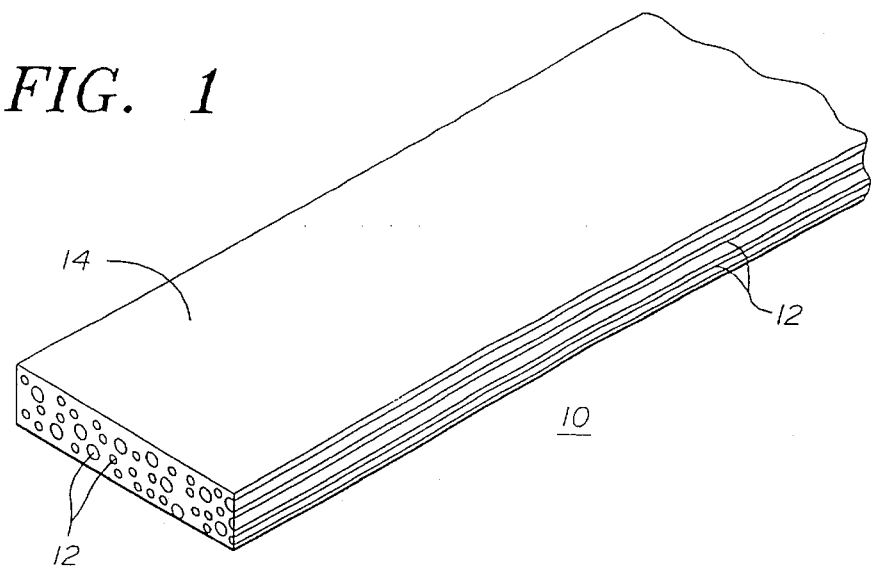
FIG. 1: is a front perspective view of a preferred unidirectional fiber reinforced thermoplastic composite tape of this invention.
Figure 2:
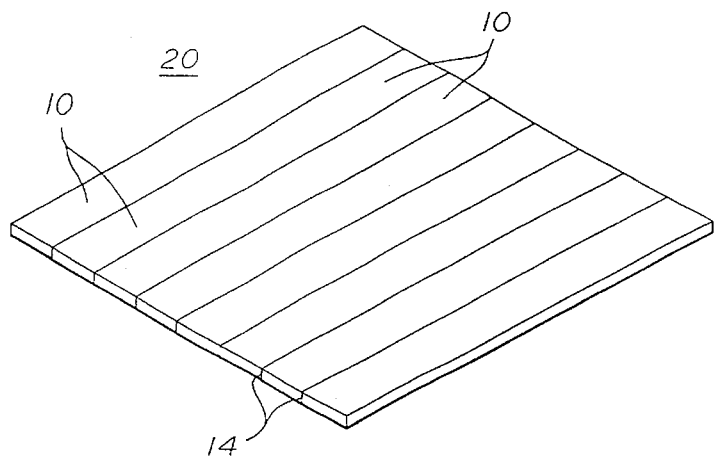
FIG. 2: is a front perspective view of a composite sheet composed of a plurality of the composite tapes of FIG. 1 which have been seamed together along their longitudinal sides.

Polymer matrix composites are provided by this invention which contain fabric facing layers disposed on thermoplastic composite cores. These composite materials can be thermoformed to provide a smooth fabric surface which is virtually free of wrinkles, kinking, and buckling. As used herein, the term "thermoplastic" refers to any polymer resinous material or blend that softens upon heating and solidifies upon cooling and can be thermoformed by application of heat and pressure. The term "fabric layer" is a relatively broad term meant to encompass both woven and nonwoven fabric layers and scrims. Finally, the term "elasticity" means the ability of a material to distort elastically as result of the construction of the material or due the inherent tensile elongation properties of the plastic or fibers used in the material.

With reference to the Figures, and particularly to FIGS. 1–3 and 6 thereof, the thermoplastic composite core of this invention will now be described. The thermoplastic composite core includes a thermoplastic matrix containing a reinforcement, preferably reinforcing fibers, and also singular layers of thermoplastics sandwiched in the composite core.

The thermoplastic matrix of the composite cores of this invention contain one or more thermoplastic resins, alloys or copolymers. Typical resins useful in this regard include acetal, acrylics, cellulosics, fluorocarbons, nylons, polyalomer, polyaryl ether, polyaryl sulphone, polycarbonate, polyethylenes, polyimide, polyphenylene sulfide, polypropylene, polystryrene, polyurethane, polyvinyl chlorides, styrene acrylonitrile, polyphenylene oxide, polysulfone, polyether sulfone, polymethylmetha acrylates, polyesters (PET, PBT), and their respective copolymers, compounds, and derivatives.

The preferred reinforcing fibers 12 of this invention are of the light-weight and high-strength high modulus variety, such as carbon, glass, aramid, metal, or ceramic fibers. These fibers are preferably uniformly distributed throughout the composite to about 10–80 vol. % and preferably at least about 30% volume. Factors that influence the fatigue resistance and tensile properties of reinforced thermoplastics include the proportion of reinforcing fibers, morphology of the reinforcement (i.e. random chopped mat, unidirectional fiber, or woven cross-ply roving), and the matrix resin. For example, in carbon-reinforced composites, fatigue, and tensile performance of chopped-mat reinforcement is significantly lower than that of a woven, cross-ply fabric.

Advanced composites, such as unidirectional carbon/thermoplastic laminates can have better fatigue resistance than steel, aluminum, or glass-reinforced composites. Compared with unidirectional laminates, the fatigue strengths of other reinforcement types in decreasing order are: 85% unidirectional, cross-ply, glass fabric, and randomly oriented short fibers. Accordingly, this invention prefers that the fibers are unidirectional and that the composite material contain a laminated structure. Discontinuous fibers more closely model the fatigue strength of the polymer matrix, making fiber-to-matrix bonding more important for optimum performance.

Presently, the preferred fibers of this invention comprise carbon, glass, such as E-glass and S-glass, boron, aramid, such as KEVLAR® 29 or KEVLAR® 49 (available from du Pont), ceramic fibers, metallic fibers, and metal coated fibers.

The above-described thermoplastic resins and reinforcing fibers can be arranged in a number of variations to produce dozens of thermoplastic-fiber composites. Some of these variations are described, along with their resulting fatigue properties, in Table I below:

TABLE I

Fatigue Strength of Reinforced Thermoplastics[1]

| Material | Glass fibers, % | Carbon fibers, % | Strength, × $10^3$ psi | |
|---|---|---|---|---|
| | | | @ $10^4$ cycles | @ $10^7$ cycles |
| Acetal Copolymer | 30 | — | 9 | 7 |
| Nylon 6[2] | 30 | — | 7 | 5.7 |
| Nylon 6/6 | — | — | 6 | 5 |
| Nylon 6/6[2] | — | — | 3.4 | 3 |
| Nylon 6/6[2] | 30 | — | 8 | 6 |
| Nylon 6/6[2] | 40 | — | 9 | 7 |
| Nylon 6/6 | 40 | — | 10.5 | 9 |
| Nylon 6/6[2] | — | 30 | 13 | 8 |
| Nylon 6/6[2] | — | 40 | 15 | 8.5 |
| Nylon 6/10[2] | 30 | — | 7 | 5.5 |
| Nylon 6/10[2] | 40 | — | 8 | 7 |
| Polycarbonate | 20 | — | 9 | 5 |
| Polycarbonate | 40 | — | 14.5 | 6 |
| Polyester, PBT | 30 | — | 11 | 5 |
| Polyester, PBT | — | 30 | 13 | 6.5 |
| Polyetheretherketone | — | 30 | 18 | 17.5 |
| Polyethersulfone | 30 | — | 16 | 5 |
| Polyethersulfone | 40 | — | 19 | 6 |
| Polyethersulfone | — | 30 | 22 | 6.7 |
| Mod. Polyphenylene Oxide | 30 | — | 7 | 4.7 |
| Polyphenylene Sulfide | — | 30 | 13 | 9.5 |
| Polysulfone | 30 | — | 14 | 4.5 |
| Polysulfone | 40 | — | 16 | 5.5 |

[1]Tests by ASTM D 671 at 1,800 cycles/min., as reported in Advanced Materials & Processes, Vol. 137, Issue 6, p. 102 (June 1990).
[2]Moisture conditioned, 50% R.H.

The thermoplastic composite core of this invention can be fabricated in a number of ways. One method is to begin with continuous rovings or bundles of fibers. The rovings are spread out to separate the filaments and then they are passed through a fluidized bed of thermoplastic resin powder. The spread fibers pick up the powder as they pass through the fluidized bed. The now resin-coated fibers are heated to the melting point of the thermoplastic resin in an oven to smoothly coat the fibers to wet them out completely, or as nearly completely as the process permits. Since the now-coated fiber bundle is in a nongeometric shape, it is then passed through a die or former to shape the bundle into a tape-like configuration. This tape preferably has a width which is much greater than its thickness. The thickness should be at least 50 μm so as to have sufficient strength to withstand mechanical working into the final thermoplastic matrix, and a preferred width of at least about 3 mm to avoid over twisting during the subsequent mechanical operations.

Alternatively, the fibers may be passed through an extrusion cross-head die containing a bath of molten thermoplastic polymer. As the fibers pass through the die, the molten polymer coats the fibers and completely wets them out. This operation could also be followed by a shaping step to configure the coated bundle of fibers into a tape configuration. Other methods include passing the fibers through a solution in which the polymer powder is suspended, or sandwiching the fiber web between films of polymer, and then passing them through heated laminated rollers under pressure and elevated temperature to coat them. Both of these fabrication methods can be additionally followed by a forming step to produce tapes.

The end result of these impregnation methods is that a tape 10 is formed in which there are continuous unidirectional fibers 12 in the axial or longitudinal direction, and that these fibers 12 are encapsulated within a thermoplastic, thermoformable matrix 14, as substantially described in FIG. 1.

Figure 3:
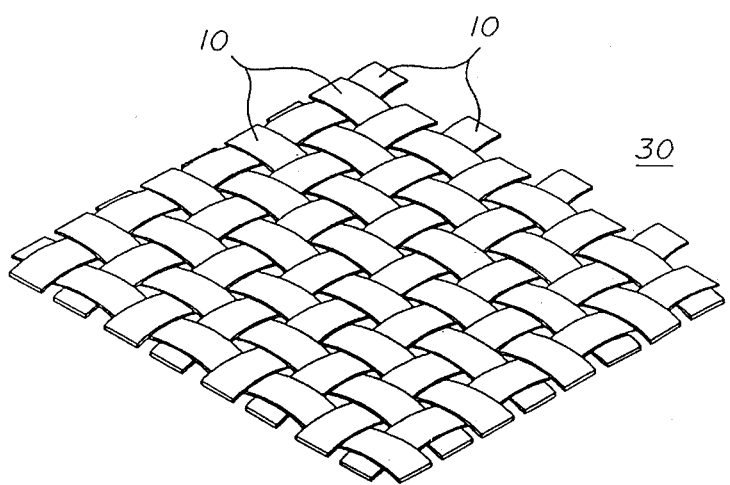
FIG. 3: is a top perspective view of an alternative composite sheet illustrating a plurality of composite tapes of FIG. 1 woven to form a fabric.

In order to produce a panel from these unidirectional fiber reinforced thermoplastic tapes 10, a plurality of tapes can be woven into sheet fabric, such as woven sheet of tape 30, shown in FIG. 3. In this woven sheet 30, the tapes 10 are oriented in the 0° and 90° direction. Such woven constructions are disclosed in U.S. Pat. No. 5,082,701, which is hereby incorporated by reference. Alternatively, the tapes can be placed adjacent to one another and seamed, attached, welded, or stitched in position before laying the next tape 10 as shown by seamed sheet 20 of FIG. 2.

In an alternative procedure for constructing panels, a "commingled fiber fabric" is produced. Fibers or thermoplastic resin and reinforcing fibers are commingled into a yarn. The commingled yarns are then woven into fabric. The fabric or layers of fabric are compression molded into a flat laminate under heat and pressure. The resin fibers melt and flow to wet out the reinforcing fibers.

In still another method, an "assembled composite" can be produced. In such a method, woven or nonwoven fabric random or directional webs of reinforcing fibers are alternately stacked with a layer of thermoplastic film or powder. This assembly is then consolidated into a laminate under heat and pressure. Also, the method described by Fitchmun, U.S. Pat. No. 4,778,717 whereby a fabric is dipped in a liquid resin may be employed.

Figure 6:
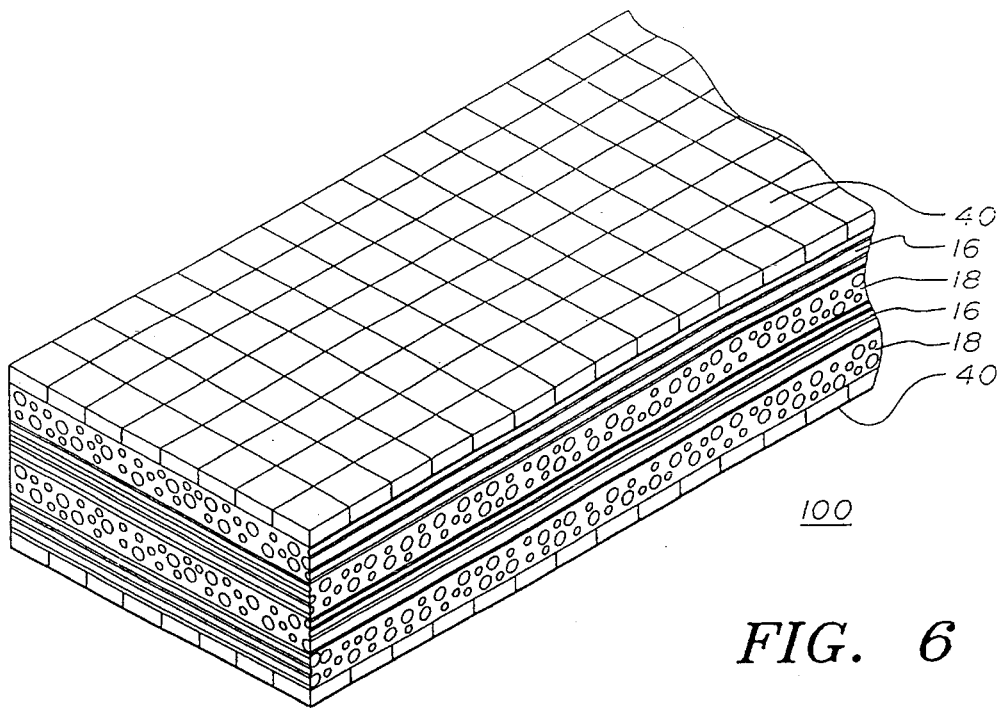
FIG. 6: is a top perspective view of a preferred polymer matrix composite of this invention including a laminated, thermoplastic composite core and a pair of fabric facing layers.
Figure 7A:
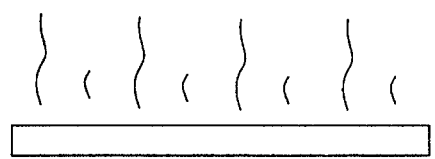
FIG. 7(a)–(d): diagrammatically illustrate a preferred thermoforming sequence for preparing molded articles pursuant to this invention.
Figure 7B:
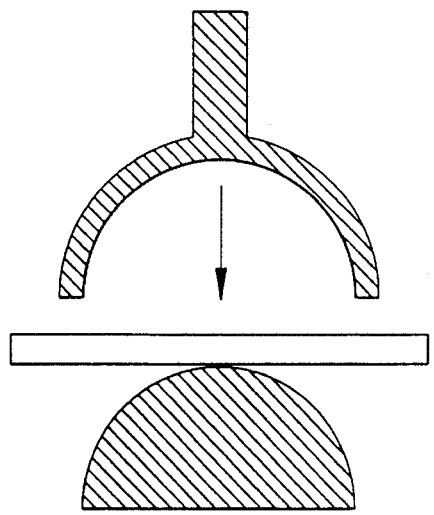
Figure 7C:
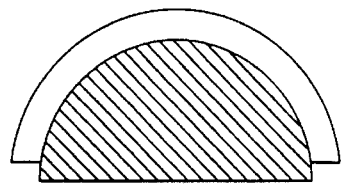
Figure 7D:
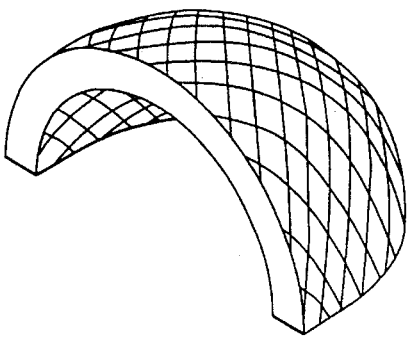

Referring to the polymer matrix composite material 100, shown in FIG. 6, it will be understood that the preferred thermoplastic composite core is produced by laminating at least two thermoplastic sheets comprising unidirectional fibers having different orientations. These sheets are desirably placed on top of one another; for instance in a 0°/90°/ 0°/90° orientation that would be functional. However, it will be understood that there are numerous orientations and ply combinations.

The sheets used in the thermoplastic composite core in this embodiment can be thermoformed to laminate them together into a integral composite. In one manufacturing sequence, the laid up sheets are placed in a compression molding press, where heat and pressure are used to consolidate the assembled sheets into a nearly void-free solid composite laminated panel. It is envisioned that both seamed sheets 20 and woven sheets 30 can be used interchangeably in the laminated construction. Alternatively, commingled fibers fabric or the assembled composite (described above) can be incorporated into the structure of the laminated composite panels.

Additionally, a thin thermoplastic film can be placed on both sides of the laminated composite, particularly if the top laminated sheets contain woven tapes, to fill in any voids resulting in the lamination of the woven pattern. The polymeric ingredients disclosed for the matrix of the thermoplastic composite core would be suitable resins for this film.

Figure 4:
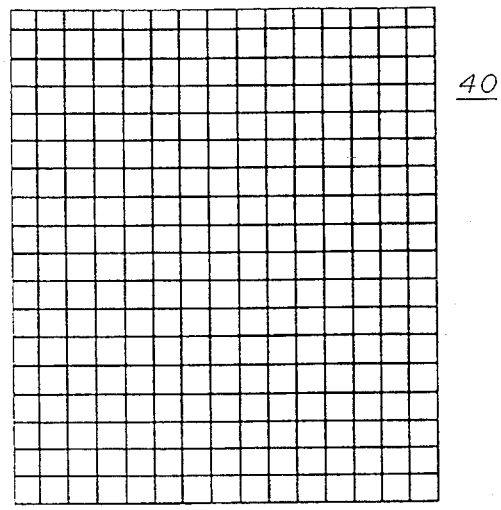
FIG. 4: is a top planar view of a reinforcing scrim.

The preferred fabric layer 40 of this invention will now be described. Although woven and nonwoven fabrics and scrims are suitable for this invention, woven fabrics are the most desirable. A fabric 40, such as that described in FIG. 4, is a nonwoven fabric, screen of bonded fibers or a woven fabric, whereby the construction permits the yarns or individual fibers to move relative to their intersection points.

The fabric layer of this invention does not necessarily need to contribute to the mechanical properties of the panel, therefore it does not have to, but may, contain high strength fibers, such as those types of fibers reinforcing the thermoplastic composite core. Instead of carbon, glass, or aramid fiber, the fabric layer 40 of this invention preferably contains ordinary, natural, or synthetic fibers, such as cotton, wool, silk, rayon, nylon, polyester, polypropylene, polyethylene, etc. The advantage of using these traditional textile fibers, is that they are available in many colors and can provide an infinite variety of patterns and textures to the preferred fabric layers. Such fibers can be woven, or spunbonded to produce nonwoven textile fabrics. Alternatively, plain color fabric can be easily dyed and printed in a variety of colors and patterns. Additionally, reinforcing fibers, such as glass, carbon, and aramid, could be used for surface fabric, provided the overall fabric construction allows sufficient elasticity.

Figure 5:
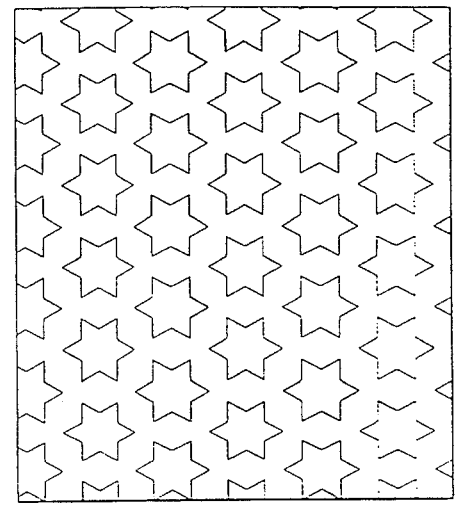
FIG. 5: is a top planar view of a printed fabric.

As described in FIG. 5, the preferred woven fabric 50 can include a printed, aesthetically appealing printed pattern. The pattern can be created by weaving different colored fibers into an ornamental design, however, this would involve using numerous yarn inputs with different colors in the warp, and complex weft inputs to obtain sophisticated patterns. A less expensive alternative would be to use commercially available patterned fabrics, which are intended for garments or furniture, etc., and apply these fabrics to the thermoplastic composite core of this invention. Accordingly, this invention prefers to employ consumer textile fabrics, imprinted with art work, logos, and trademarks which are printed, dyed, or silk screened onto the fabric.

The fabric layers of this invention are preferably bonded to the resin-containing thermoplastic composite core with a "resinous adhesive" e.g. film, powder, or tacky material used to bond the fabric to the core. One preferred method of applying the fabric layer to the core is to prepare a thin film, 10 μm to 500 μm thick, made from a compatible thermoplastic resin as the matrix of the thermoplastic composite core. This film can be placed over the core and the fabric layer is then placed onto this film. Another film of the same or similar composition is preferably applied to the top of the fabric. The assembly including the core, fabric layer, and the layers of thermoplastic film is then placed into a compression molding press which subjects the components to elevated heat and pressure. The films, fabric, and core are thereafter consolidated and fused into an integral panel shape. The total amount of film needed to fully bond, incorporate, and/or cover the fabric depends upon the thickness, porosity, and texture or the fabric. As a rule of thumb, the total film thickness should be about 0.3 to about 3.0 times the thickness of the fabric. One may use more film below or above the fabric to impart aesthetic appearances, e.g., texture, depth, etc.

In the most preferred construction, the fabric layer weave and the fiber construction of the core are chosen so that the melted film resin flows through the interstices in the fabric layer weaving to anchor the fabric to the panel. Additionally, the fibers of the fabric layer can be intertwined and bonded closely with the fibers of the core to increase the adhesion of the fabric layer to the core. It is further envisioned that the thermoplastic film can be substituted by an evenly distributed resin powder or a suitable adhesive to achieve the same result. The fabric, thus applied to one or both planar surfaces of the panel-like core, becomes the outermost layer of the composite material, and acts to overcome the problems of wrinkling, and a lack of an aesthetic appearance usually associated with conventional composite materials.

The polymer matrix composite materials of this invention are thermoformable, and can be used to produce molded articles ranging from suitcases to shoe supports. Referring to FIG. 7, a thermoforming method for producing a safety shoe toe protector is diagrammatically described. The composite material is heated in step 7(a), followed by placing the heated material onto a mold in step 7(b). Under heat and pressure, for example using vacuum forming or compression molding, the mold conforms the heated composite material to a given shape in step 7(c). In step 7(d), the die is opened, and the finished, thermoformed part—in this case, a safety shoe toe protector—is removed and cooled.

From the foregoing, it will be understood that this invention provides polymer matrix composites having a bonded fabric layer which can be thermoformed without wrinkling or distortion. The difference in the elasticity between the fabric layer and the thermoplastic composite core of this invention is sufficient so that when the mold is applied to thermoform the composite material, the fabric layer stretches to conform smoothly to the core over contours and the like. Although various embodiments have been illustrated, this was for the purpose of describing, and not limiting the invention. Various modifications will become apparent to one skilled in the art, and are considered within the scope of the attached claims.

What is claimed is:

1. A polymer matrix composite material suitable for thermoforming to form a molded article, comprising a fiber-reinforced thermoplastic composite core and fabric layer integrally bonded to said core, said fabric layer having greater elasticity than said core, so that said fabric layer can conform smoothly to said core during thermoforming.

2. The composite material of claim 1, wherein said thermoplastic composite core comprises at least two laminated thermoplastic layers comprising unidirectional fibers having different orientations.

3. The composite material of claim 2, wherein at least one of said laminated layers comprises: woven or seamed thermoplastic tapes containing unidirectional fibers, comingled fiber fabric, an assembled composite, or fabric made by impregnation of liquid resins.

4. The composite material of claim 1, wherein said fibers are selected from the group comprising carbon, glass, boron, aramid, metals, ceramics, and mixtures thereof.

5. The composite material of claim 1, wherein said thermoplastic composite core comprises one or more of the resins selected from: acetal, acrylics, cellulosics, fluorocarbons, nylons, polyallomer, polyaryl ether, polyaryl sulphone, polycarbonate, polyethylenes, polyimide, polyphenylene sulfide, polypropylene, polystryrene, polyurethane, polyvinyl chlorides, styrene acrylonitrile, polyphenylene oxide, polysulfone, polyether sulfone, polymethylmethacrylates, polyesters (PET, PBT), and their respective copolymers, compounds, and derivatives.

6. The composite material of claim 1, wherein said thermoplastic composite core comprises a pair of fabric layers integrally bonded with a thermoplastic resin or a resinous adhesive to opposing surfaces of said thermoplastic composite core.

7. The composite material of claim 1, wherein said fabric layer has at least 5% greater elasticity than said thermoplastic composite core.

8. The composite material of claim 7, wherein said fabric layer comprises a woven or printed pattern.

9. The composite material of claim 1, comprising at least about 10 vol. % fibers.

10. A polymer matrix composite material for thermoforming to form a molded article, comprising:
    a thermoplastic composite core comprising at least two laminated thermoplastic layers, including unidirectional fibers having a first and second orientation; and
    a woven fabric layer bonded to said core by a resinous adhesive, said woven fabric layer being more elastic than said core so that upon thermoforming, said fabric layer conforms smoothly to said core without wrinkling.

11. The composite material of claim 10, wherein said laminated thermoplastic layers comprise a plurality of unidirectional tapes, woven and nonwoven fabrics, or tow prepegs in a thermoplastic matrix.

12. The composite material of claim 10, wherein at least a first of said laminated thermoplastic composite layers comprises: a plurality of unidirectional tapes comprising longitudinally disposed filaments in a thermoplastic matrix, a commingled fiber fabric, woven tapes, an assembled composite, or a fabric made by impregnation of liquid resin.

13. The composite material of claim 12, wherein said plurality of unidirectional tapes comprise a width greater than their thickness.

14. The composite material of claim 13, wherein said unidirectional tapes are laminated together in a side-by-side relationship to provide said first laminated thermoplastic sheet, wherein said filaments are aligned in substantially a single orientation.

15. The composite material of claim 14, wherein said filaments comprise glass, boron, aramid, or carbon, metallic, or ceramic fibers.

16. The composite material of claim 12, wherein a second of said laminated thermoplastic layers comprises a plurality of unidirectional tapes containing longitudinal filaments.

17. The composite material of claim 10, wherein said woven fabric layer comprises a woven or printed pattern.

18. The composite material of claim 10, comprising about 10–80 vol. % fibers.

19. The composite material of claim 10, wherein said resin or resinous adhesive is provided by a resin powder or film precursor.

20. A polymer matrix composite material suitable for thermoforming to form a molded article, comprising a thermoplastic composite core comprising a plurality of laminated thermoplastic sheets thermomolded together, each of said sheets comprising unidirectional fibers oriented in substantially a single direction, said sheets layered to provide a plurality of orientations to said fibers in said composite material; and a woven fabric having an aesthetic pattern bonded to said core by a thermoplastic resin or resinous adhesive, said woven fabric having at least about 5% greater elasticity than said core so that upon thermoforming, said woven fabric layer conforms smoothly to said core without wrinkling or distorting.

21. A method of manufacturing a thermomoldable, polymer matrix composite, comprising:

providing a fiber-reinforced laminated thermoplastic composite core having a first surface thereon; and adhering a fabric layer having a greater elasticity than said core to said first surface, said composite containing at least 10 vol. % fibers, and said fabric layer conforming smoothly to said core during thermoforming without substantial wrinkling or distorting.

22. A method of forming a molded article, comprising thermomolding the composite material of claim 8 with heat and pressure into a finished article.

23. A method of forming a molded article, comprising preparing a polymer matrix composite according to claim 22; and subjecting said composite to heat and pressure to form a finished article.

* * * * *